United States Patent [19]

Munro et al.

[11] Patent Number: 5,360,906
[45] Date of Patent: Nov. 1, 1994

[54] PESTICIDAL COMPOUNDS

[75] Inventors: David Munro, Maidstone; Bipin Patel, Sittingbourne, both of England

[73] Assignee: Shell Research Limited, London, England

[21] Appl. No.: 157,788

[22] Filed: Nov. 23, 1993

Related U.S. Application Data

[62] Division of Ser. No. 15,757, Feb. 10, 1993.

[30] Foreign Application Priority Data

Feb. 14, 1992 [EP] European Pat. Off. ........ 92301212.4

[51] Int. Cl.⁵ .................. C07D 239/06; C07D 239/12; C07D 261/06
[52] U.S. Cl. ..................................... 544/331; 544/333; 548/247
[58] Field of Search ................. 548/247; 544/331, 333

[56] References Cited

U.S. PATENT DOCUMENTS 4,803,277  2/1989  Shiokawa et al. .
4,882,344  11/1989 Shiokawa et al. .
4,988,712  1/1991  Shiokawa et al. .
5,204,360  4/1993  Shiokawa et al. .

OTHER PUBLICATIONS

CA 106(5):28848p Heterocyclic compounds. Shiokawa et al., p. 169, 1987.
CA 118(17):163054g Imidacloprid . . . activity. Moriya et al., p. 290, 1993.
Biosci. Biotech. Biochem. 57(1) pp. 127–128, Structural . . . Activity, Moriya et al, 1993.
"Pharmacology" by C. Paul, *Chemical Abstracts,* vol. 115, No. 1, Jul. 8, 1991, p. 326, Yamada et al., Preparation of isoxazoles as insecticides.

*Primary Examiner*—Mary C. Lee
*Assistant Examiner*—Joseph K. McKane

[57] ABSTRACT

Compounds of the formula:

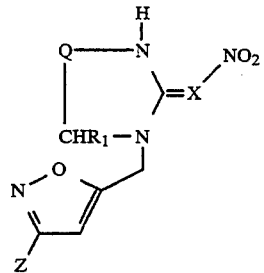

wherein
  $R^1$ is hydrogen or alkyl;
  Q is a linkage group of the formula —$CHR^2$— or —$CHR^3$—$CHR^4$—where $R^2$ is hydrogen or alkyl, $R^3$ is hydrogen or alkyl, and $R^4$ is hydrogen or alkyl;
  X is nitrogen or =CH—; and
  Z is halogen, show insecticidal activity. Also disclosed are the processes for producing the compounds and methods of using them as insecticides.

4 Claims, No Drawings

PESTICIDAL COMPOUNDS

This is a divisional application of Ser. No. 08/015,757 filed Feb. 10, 1993 entitled Pesticidal Compounds.

FIELD OF THE INVENTION

This invention relates to novel isoxazolylmethyl substituted heterocyclic compounds, to their use as pesticidal, especially insecticidal, agents, to pesticidal compositions containing such compounds, and to a process for the preparation of such compounds. The invention relates in particular to N-(3-halo-5-isoxazolylmethyl)-2-nitromethylene- and -2-nitroimino imidazolines and pyrimidines.

BACKGROUND OF THE INVENTION

European Patent Application No. EP-A-0192060 (Nihon) relates to heterocyclic compounds of a general formula

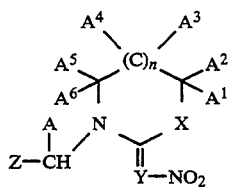

wherein:
- n is 0 or 1; $A^1$, $A^2$, $A^5$ and $A^6$ independently are hydrogen or alkyl; $A^3$ and $A^4$ independently are hydrogen, hydroxy or alkyl;
- X is sulfur, oxygen, -N-$A^7$ or -N-$A^8$, wherein $A^7$ is selected from a large group comprising, for example, hydrogen, halogen, hydroxy, alkoxy, benzyloxy or alkyl, and wherein $A^8$ is selected from hydrogen, alkyl, aryl, or benzyl;
- Y is nitrogen or

wherein $A^9$ is selected from a large group comprising, for example, hydrogen, halogen, hydroxy, alkoxy, benzyloxy, or alkyl;
- A is hydrogen or alkyl;
- Z is a 5 or 6 membered heterocyclic group containing at least one heteroatom selected from oxygen, sulfur or nitrogen and at least one substituent selected from a large group comprising, for example, halogen, alkyl, haloalkyl, nitro, cyano, alkoxy, alkylthio, alkylsulfinyl, alkylsulfonyl, alkenyl, haloalkoxy, haloalkylthio, haloalkenyl, acylamino, haloacylamino, alkoxycarbonyl, thiocyanato or alkynyl.

EP-A-0192060 purports to disclose 887 compounds but only a relatively few are accompanied by any physico-chemical data showing that they have been prepared.

The broad claims of EP-A-0192060 embrace the N-(3-halo-5-isoxazolylmethyl-2-nitromethylene- and 2-nitroimino imidazolines and pyrimidines of the present invention. Furthermore, three such compound structures are illustrated, on page 164, as Examples 522-524, as are several other 3-substituted-5-isoxazolylmethyl analogs, by means of a general formula and a tabular listing.

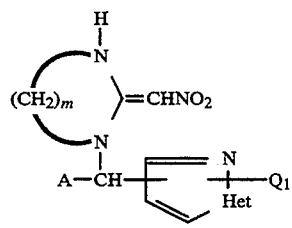

However, there are no analytical or biological data provided with regard to such compounds and there is no indication that the compounds 522-524 were actually prepared or evaluated.

N-(3-Halo-5-isoxazolylmethyl)-2-nitromethylene- and -2-nitroimino imidazolines and pyrimidines and the properties thereof are therefore not properly enabled by the disclosure of EP-A-0192060.

The 3-methyl and 3-trifluoromethyl-5-isoxazolylmethyl compounds which are Examples 6, 519, and 529 in the Nihon application and which evidently were prepared have been made and tested but have been found to be less active in combating certain undesired pests than corresponding 3-halo-5-isoxazolyl compounds of the present invention.

DESCRIPTION OF THE INVENTION

According to a first aspect of the present invention, there is provided a compound of general formula

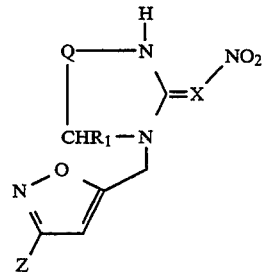

wherein
- $R^1$ is hydrogen or alkyl;
- Q is a linkage group of the formula —$CHR^2$— or $CHR^3$—$CHR^4$— where $R^2$ is hydrogen or alkyl, $R^3$ is hydrogen or alkyl, and $R^4$ is hydrogen or alkyl;
- X is nitrogen or =CH—; and
- Z is halogen.

An alkyl group as referred to above is preferably a $C_{1-4}$ alkyl group, more preferably a methyl group.
$R^2$ preferably is hydrogen or methyl and most preferably is hydrogen.
$R^3$ preferably is hydrogen.
$R^4$ preferably is hydrogen.
Preferably, Q is —$CHR^2$— where $R^2$ is as defined above.
Preferably, X is =CH—.
Preferably, Z is bromine or chlorine, most preferably chlorine.

In accordance with a second aspect of the present invention there is provided a process for the preparation of a compound of general formula I, which comprises reacting a compound of general formula

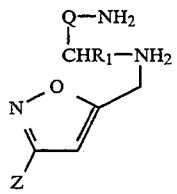

(II)

with a compound of the general formula

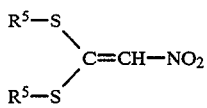

(III)

or with a compound of the formula

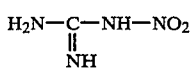

(IV)

wherein Z, $R^1$ and Q are defined above, and the groups $R^5$ independently are $C_{1-4}$ alkyl or benzyl. Preferably both groups $R^5$ are identical $C_{1-4}$ alkyl groups, most preferably methyl.

The reaction suitably takes place in an inert solvent, and at an elevated room temperature. When a reactant of general formula III is employed, to make a nitromethylene compound of general formula I, the solvent is suitably an alkanol, for example ethanol or methanol. The reaction suitably takes place at an elevated temperature, preferably at the reflux temperature. When a reactant of general formula IV is employed, to make a nitroimino compound of general formula I, the solvent is suitably water. The reaction suitably takes place at an elevated temperature, preferably from about 70° C. to about 90° C.

A compound of general formula II is prepared by reaction of a compound of general formula

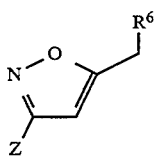

(V)

with a compound of general formula

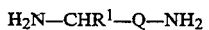

(VI)

where Z, $R^1$ and Q are as defined above and $R^6$ is halogen, preferably chlorine or bromine, and most preferably bromine. This reaction suitably takes place in a polar organic solvent, for example acetonitrile. The reaction temperature is preferably from about 0° C. to about 40° C.

Compounds of general formula II are novel and they, and the process for their preparation, constitute further aspects of the present invention.

A compound of general formula V is prepared by providing a reaction mixture comprising a compound of general formula

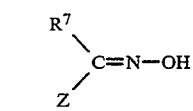

(VII)

an alkali metal base, and a compound of general formula

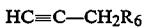

(VIII)

wherein Z and $R^6$ are as defined above and $R^7$ is halogen, preferably chlorine or bromine. Preferably $R^7$ and Z are identical. Suitably, the reaction takes place in an inert organic solvent, for example an aromatic hydrocarbon such as toluene, an ester such as ethyl acetate, a halogenated alkane such as dichloromethane, or an ether such as dimethyl ether. The reaction preferably takes place at a temperature from about 0° C. to about 50° C.

A compound of general formula VII is prepared by controlled halogenation of glyoxylic acid aldoxime. Halogenation is suitably achieved by a means of a calculated quantity of N-chlorosuccinimide, N-bromosuccinimide or t-butyl hypochlorite in an inert solvent, suitably an ether such as dimethyl ether, or by means of molecular chlorine or bromine, suitably in an inert solvent, for example a halogenated hydrocarbon such as dichloromethane. The reaction temperature is suitably from about 0° C. to about 30° C. except when N-chlorosuccinimide is employed when a temperature from about 50° C. is suitable. Preferably the compound of general formula VII is used in the next step without isolation to form the compound of general formula With respect to the preparation of compounds of general formula V, reference is made to Synthetic Communications, 18(10), p. 1171-1176 (1988).

The compounds of the general formula I exhibit pesticidal, for example insecticidal, activity. Accordingly, the invention also provides an insecticidal composition comprising a compound of the general formula I together with at least one carrier. The invention further provides a method of combating insects at a locus, which comprises applying to the locus an insecticidal compound or composition according to the invention. The compounds of the general formula I are of particular interest in combating aphids, especially pea aphids Acyrthosiphon pisum and black bean aphids Aphis fabae, rice hoppers, especially Nephotettix cincticeps and Nilaparvata lugens, and whiteflies Trialeurodes vaporariorum. The compound N-(3-chloro-5-isoxazolylmethyl)-2-nitromethylene imidazoline shows particularly interesting activity against such insects.

A carrier in a composition according to the invention is any material with which the active ingredient is formulated to facilitate application to the locus to be treated, or to facilitate storage, transport or handling. A carrier is solid or liquid, including a material which is normally gaseous but which has been compressed to form a liquid, and any of the carriers normally used in formulating biocidal compositions are useful. Preferably compositions according to the invention contain from about 0.5% to about 95% by weight of active ingredient.

Suitable solid carriers include natural clay and silicates including natural silicas such as diatomaceous earths; magnesium silicates, for example talcs; magnesium aluminum silicates, for example attapulgites and vermiculites; aluminum silicates, for example kaolinites, montmorillionites and micas; calcium carbonate; calcium sulfate, ammonium sulfate; synthetic hydrated silicon oxides and synthetic calcium or aluminum silicates; certain elements, for example carbon and sulfur; natural and synthetic resins, for example coumarone resins, polyvinyl chloride, and styrene polymers and copolymers; solid polychlorophenols; bitumen; waxes; and solid fertilizers, for example superphosphates.

Suitable liquid carriers include water; alcohols, for example isopropanol and ethylene glycols; ketones, for example acetone, methyl ethyl ketone, methyl isobutyl ketone and cyclohexanone; ethers, aromatic hydrocarbons, for examples benzene, toluene and xylene; petroleum fractions, for example kerosine and light mineral oils; chlorinated hydrocarbons, for example carbon tetrachloride, perchloroethylene and trichloroethane. Mixtures of different liquids are also suitable.

Compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent and it may be non-ionic or ionic. Examples of suitable surface-active agents include the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these fatty acids with ethylene oxide and/or propylene oxide; condensation products of fatty alcohols or alkyl phenols, for example p-octylphenol or p-octylcresol, with ethylene oxide and/or propylene oxide; sulfates or sulfonates of these condensation products; alkali or alkaline earth metal salts, preferably sodium salts of sulfuric or sulfonic acid esters containing at least 10 carbon atoms in the molecule, for example sodium lauryl sulfate, sodium secondary alkyl sulfates, sodium salts of sulfonated castor oil, sodium alkylaryl sulfonates such as dodecylbenzene sulfonate; and polymers of ethylene oxide and copolymers of ethylene oxide and propylene oxide.

The compositions of the invention are for example formulated as wettable powders, dusts, granules, solutions, emulsifiable concentrates, emulsions, suspension concentrates and aerosols. Wettable powders usually contain 25%, 50% or 75% w of active ingredient and usually contain in addition to solid inert carrier 3%-10% w of a dispersing agent and, where necessary, up to 10% w of stabilizer(s) and/or other additives such as penetrants. Dusts are usually formulated as a dust concentrate having a similar composition to that of a wettable powder but without a dispersant, and are diluted in the field with further solid carrier to give a composition usually containing 0.5% to 10% w of active ingredient. Granules are usually prepared to have a size between 10 BS mesh and 100 BS mesh (1.676 mm–0.152 mm), and are manufactured by agglomeration or impregnation techniques. Generally, granules will contain 0.5% to 75% w active ingredient and up to 10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10% to 50% w/v active ingredient, 2%–20% w/v emulsifiers and up to 20% w/v of other additives such as stabilizers, penetrants and corrosion inhibitors. Suspension concentrates are usually compounded so as to obtain a stable, non-sedimenting flowable product and usually contain 10% to 75% w active ingredient, 0.5% to 15% w of dispersing agents, 0.1% to 10% w of suspending agents such as protective colloids and thixotropic agents, up to 10% w of other additives such as defoamers, corrosion inhibitors, stabilizers, penetrants and water or an organic liquid in which the active agent is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The composition of the invention may also contain other ingredients, for example other compounds possessing herbicidal, insecticidal or fungicidal properties.

The invention will now be described further with reference to the following Examples.

EXAMPLE 1

Preparation of N-(3-chloro-5-isoxazolylmethyl)-2-nitromethylene imidazoline 1.a. Preparation of glyoxylic acid aldoxime Hydroxylamine hydrochloride (42 g) was added to a solution of glyoxylic acid hydrate (50 g) in water (150 ml) and the reaction mixture was stirred overnight. It was then extracted using diethyl ether three times (150 ml each time) and the solvent was removed by evaporation to yield glyoxylic acid aldoxime as a colorless solid (63 g). After recrystallization from acetonitrile, the m.p. was 140° C.

| Analysis  | % C  | % H | % N  |
|-----------|------|-----|------|
| Required: | 27.0 | 3.4 | 15.7 |
| Found:    | 26.8 | 3.4 | 25.7 |

1.b. Preparation of 3-chloro-5-bromomethylisoxazole

N-chlorosuccinimide (26.8 g) was added in portions to glyoxylic acid aldoxime (9.2 g) in dimethyl ether (100 ml) at 55° C.–57° C. to form dichloroformaldoxime which was used directly in the next step. Propargyl bromide in toluene (50 ml at 80% concentration) was added followed by potassium bicarbonate (40 g), and the reaction mixture was stirred at ambient temperature for 48 hours. The reaction mixture was then faltered, all solvent was removed in vacuo, and the residue was dissolved in trichloromethane. Thin layer chromatography gave 3-chloro-5-bromomethylisoxazole as a pale yellow oil (11.8 g), which was used directly in the next step. The identity of this product was confirmed by mass spectrometry.

1.c. Preparation of N-(3-chloro-5-isoxazolylmethyl)-2-nitromethylene imidazoline Ethylenediamine (10 g) was dissolved in acetonitrile (30 ml), and a solution of 3-chloro-5-bromomethylisoxazole (11.3 g) in acetonitrile (10 g) was added dropwise at 10° C.-15° C. The reaction mixture was then allowed to reach ambient temperature over 1 hour, decanted from a gummy precipitate and the acetonitrile removed by evaporation to give an orange oil, N-(3-chloroisoxazolylmethyl)ethylene diamine. The orange oil (8.7 g) was dissolved in ethanol (20 ml) and added to a suspension of 1-nitro-2,2-bis(methylthio)ethylene (8 g) in ethanol (50 ml) and the reaction mixture refluxed, with stirring, until evolution of methylmercaptan ceased (about 1½ hours). Thin layer chromatography indicated two products. The solvent was removed in vacuo, and the residue thin-layer chromatographed to give the title compound as a colorless solid (5.9 g), m.p. after recrystallization was 173° C.

| Analysis | % C | % H | % N |
|---|---|---|---|
| Required: | 39.3 | 3.7 | 23.0 |
| Found: | 39.7 | 3.8 | 23.0 |

EXAMPLE 2

Preparation of N-(3-bromo-5-isoxazolylmethyl)-2-nitromethylene imidazoline 2.a. Preparation of dibromoformaldoxime To a stirred solution of glyoxylic acid (100 g) in water (800 ml) was added hydroxylamine hydrochloride (95 g) and the solution was stirred for 24 hours at ambient temperature. Sodium bicarbonate (235 g) was then carefully added, followed by dichloromethane (1 liter). To the two-phase mixture, well stirred, at 6° C., was added bromine (97 ml in 500 ml dichloromethane) at such a rate that the temperature of the mixture did not rise above 10° C. Upon completion of the addition of the bromine, the solution was further stirred for 3 hours, cooled, and the organic layer separated. The aqueous layer was extracted with dichloromethane (1 liter). The combined organic phases were dried, filtered and evaporated to leave dibromoformaldoxime as a colorless solid (160 g).

2.b. Preparation of 3-bromo-5-bromomethylisoxazole

A solution of dibromoformaldoxime (160 g) in ethyl acetate (60 ml) was added over 5 hours to a stirred solution of propargyl bromide (200 g) and potassium bicarbonate (90 g) in ethyl acetate (750 ml) containing water (10 ml). After 18, hours, water (300 ml) was added. The organic layer was separated and dried. The solvent was removed in vacuo to leave a brown oil. Thin layer chromatography showed this oil to contain only one predominant product, which was separated by thin layer chromatography giving a colorless oil (55 g) of the correct mass spectrometry M+ value for 3-bromo-5-bromomethylisoxazole.

2.c. Preparation of N-(3-bromo-5-isoxazolylmethyl)-2-nitromethylene imidazoline 3-bromo-5-bromomethylisoxazol (20 g) in acetonitrile (30 ml) was added at 10° C. to ethylene diamine (13 g) in acetonitrile (70 ml). After 1 hour the reaction mixture was decanted from a solid brown precipitate, and the solvent removed to give a brown oil (16 g), N-(3-bromo-5-isoxazolylmethyl)ethylenediamine. 12 Grams of the crude oil in ethanol (20 ml) was added dropwise to a refluxing solution of 1-nitro-2,2,-bis(methylthio)ethylene (7 g) in ethanol (80 ml). After addition the reaction mixture was refluxed for 1 hour. Thin layer chromatography indicated complete reaction, with two products. Most of the ethanol was removed in vacuo, an the residue was thin-layer chromatographed to give a colorless solid (4.1 g). After recrystallization, the m.p. was 202° C.

| Analysis | % C | % H | % N |
|---|---|---|---|
| Required: | 33.2 | 3.1 | 19.4 |
| Found: | 33.3 | 3.2 | 19.3 |

EXAMPLE 3

Preparation of N-(3-bromo-5-isoxazolylmethyl)-2-nitroimino imidazoline

N-(3-bromo-5-isoxazolylmethyl)ethylene diamine (4 g), prepared as described above, and nitroguanidine (2.5 g), were added to water (50 ml) and the reaction mixture stirred at 80° C. for 1 hour. The reaction mixture was partitioned with trichloromethane and the organic layer was separated, washed and dried. Thin layer chromatography showed a single product and was used to recover the product as a colorless solid (2.1 g). Recrystallization gave the title compound as colorless crystals (m.p. 149° C.).

| Analysis | % C | % H | % N |
|---|---|---|---|
| Required: | 29.0 | 2.8 | 24.1 |
| Found: | 29.3 | 2.9 | 24.2 |

Further compounds presented as Examples 4 to 9 below, were prepared according to procedures analogous to those described above. Comparison compounds, presented as Examples C10–C11 (not of the invention) not having chlorine or bromine substitution at the 3 position of the isoxazolyl ring were also prepared. These comparison compounds correspond to Examples 519 and 529 in EP-A-0192060, which Examples are disclosed therein as having been prepared. Data on all of the compounds are set out in Table 1 below. In Table 1, reference is made to a compound of general formula I as set forth above.

TABLE 1

| Example No. | Z | X | Q | R¹ | Analysis CHN Required % Found % | | | m.p. (°C.) |
|---|---|---|---|---|---|---|---|---|
| 4 | Cl | N | —CH₂— | H | 34.2 | 3.3 | 28.5 | 136 |
|   |   |   |   |   | 34.6 | 3.4 | 28.9 |   |
| 5 | Cl | CH | —(CH₂)₂— | H | 41.8 | 4.3 | 21.7 | 228 |
|   |   |   |   |   | 41.7 | 4.4 | 21.5 |   |
| 6 | Cl | N | —(CH₂)₂— | H | 37.0 | 3.9 | 27.0 | 228 |
|   |   |   |   |   | 37.2 | 3.9 | 27.2 |   |
| 7 | Br | CH | —(CH₂)₂— | H | 35.6 | 3.6 | 18.5 | 218 |
|   |   |   |   |   | 35.6 | 3.5 | 18.3 |   |
| 8 | Br | N | —(CH₂)₂— | H | 31.6 | 3.3 | 23.0 | 197 |
|   |   |   |   |   | 32.1 | 3.5 | 23.2 |   |
| 9 | Cl | CH | —(CHCH₃)— | H | 41.8 | 4.3 | 21.7 | 175 |
|   |   |   |   |   | 42.3 | 4.6 | 20.9 |   |
| C10 | CH₃ | CH | —(CH₂)₂— | H | 50.4 | 5.9 | 23.5 | 202 |
|   |   |   |   |   | 49.8 | 5.8 | 23.5 |   |
| C11 | CF₃ | CH | —(CH₂)₂— | H | 41.1 | 3.8 | 19.2 | 180 |
|   |   |   |   |   | 41.8 | 4.0 | 19.3 |   |

EXAMPLE 12

Pesticidal Activity

Pesticidal activity of compounds of the invention and of the comparison compounds was assessed against various forms of the following pests:

*Spodoptera littoralis* (Egyptian cotton leafworm)
*Aedes aegypti* (yellow fever mosquito)
*Musca domestica* (housefly)
*Aphis fabae* (black bean aphid)
*Acyrthosiphon pisum* (pea aphid)
*Megoura viciae* (vetch aphid)
*Phaedon cochleariae* (mustard beetle)
*Trialeurodes vaporariorum* (greenhouse whitefly)
*Nephotettix cincticeps* (green leaf hopper)
*Nilaparvata lugens* (brown rice plant hopper)

The test methods employed for each species appear below. In each test, unless otherwise stated, solutions or suspensions of test compound were made up over a range of concentrations in water (initially 0.1% w) containing 10% w acetone and 0.025% w TRITON X-100 surface active agent (the condensation product of ethylene oxide with an alkyl phenol). These solutions were sprayed at a rate equivalent to 340 liters per hectare ($3.4 \times 10^{-5}$ m$^3$/m$^2$) onto Petri dishes containing either the test species per se or diet onto which test species were subsequently introduced, as indicated. In some assays leaf discs infested with test species were sprayed while other assays involved spraying of plants which were infested subsequently with test species after the spray solution had dried. The tests were all conducted under normal insectary conditions (23° C. ±2° C., fluctuating humidity and light).

Mortality assessments were made as indicated below, in terms of percentage mortality figures. In each test a LC$_{50}$ (the dosage of active material required to kill half of the test species) for the compound was calculated from the mortality figures and compared with the corresponding LC$_{50}$ for a standard insecticide, ethyl parathion, in the same test. The results are expressed as toxicity indices thus:

$$\text{toxicity index} = \frac{\text{LC}_{50} \text{ (parathion)}}{\text{LC}_{50} \text{ (test compound)}} \times 100$$

(i) *Spodoptera littoralis* (foliar) (Sl fol)

Test solutions were sprayed as described above onto Petri dishes containing 9 cm discs of Chinese cabbage leaves on filter papers. After drying, each dish was infested with ten 2nd instar larvae. Mortality assessments were made 24 hours after infestation.

(ii) *Spodoptera littoralis* (ovicidal) (Sl OA) Test solutions were sprayed as described above onto Petri dishes containing filter papers on which were approximately fifty 24 hour old eggs. After 6 days the numbers of hatched and unhatched eggs were counted and percentage mortality calculated.

(iii) *Aedes aegypti* (Aa) Early 4th instar larvae were used. Test solutions were made up to 0.5 ppm of test compound (and progressive half-dilutions) in water containing 0.04% w TRITON X-100; acetone was initially present to aid solution, but was allowed to evaporate before introduction of larvae. Ten early 4th instar larvae were place in 100 ml of test solution held at 28° C., and after 48 hours larval mortality was recorded (Aa-2d). The final mortality was assessed by counting the number of emerged adult mosquitoes after one week (Aa-7d).

(iv) *Musca domestica* (Md)

Baths of ten 2 to 3 day old milk fed adult female houseflies, anaesthetized using carbon dioxide, were placed on filter papers inside Petri dishes. The dishes were sprayed with the test solutions as described above. The flies were retained in the Petri dishes and were fed with a dilute milk solution which was dripped down the side of the Petri dish and absorbed by the filter paper. Mortality was assessed after 24 hours.

(v) *Aphis fabae* (Af)

Tests were carded out on adult black bean aphids (Aphis fabae). Pairs of broad bean leaves on filter paper in Petri dishes were sprayed side by side with uncounted quantities of aphids in small gauze-covered containers. After passing through the spray ten aphids were tipped onto the leaves and lids were placed on the Petri dishes. Mortality was assessed after 24 hours.

(vi) *Acyrthosiphon pisum* (Ap)

Tests were carried out on young adult pea aphids. Whole pea plants 6 days after germination were placed on filter papers in Petri dishes. Ten aphids were transferred to each pea plant and left for 30 minutes to allow the aphids to settle and start to feed. The dishes were then sprayed with the test solutions as described above and lids were placed on the Petri dishes. Mortality was assessed after 24 hours.

(vii) *Megoura viciae* (Mv)

Test were carried out on adult Vetch aphids in the same way as for black bean aphids in (v) above.

(viii) *Phaedon cochleariae* (Pc)

Test solutions were sprayed as described above onto Petri dishes containing 9 cm of Chinese cabbage leaves on filter papers. After drying, each dish was infested with ten adult mustard beetles (up to 1 week old). Mortality assessments were made 24 hours after infestation.

(ix) *Trialeurodes vaporariorum* (Tv)

French bean plants (*Phaseolus vulgaris*) with two fully expanded leaves were placed in a breeding culture of *T. vaporariorum*, also on French bean plants, which were then disturbed to ensure resettlement on the introduced plants. During the subsequent 24 hour period, eggs were deposited and kept at 27° C., with a 14 hour photo period. All adult whiteflies were then carefully removed, leaving egg samples of a known age. After eight days the majority of eggs had hatched. Leaf discs containing the newly hatched nymphs were then cut from the leaves and transferred to moist filter paper. The discs were examined under a low-powered microscope to determine the exact number of 1st instar nymphs per disc and to remove any unhatched eggs. On average, 70–100 nymphs were found per disc. The discs were transferred into Petri dishes and sprayed with test solutions as described above. After 6 days percentage mortalities were assessed.

(x) *Nephotettix cincticeps* (Nc)

Tests were carded out on young adult female green leaf hoppers. Plant pots, each containing five rice seedlings 10 to 15 cm tall arranged across the center of the pot, were sprayed with test solutions as described above (but initial test concentration 0.05% of test compound). Spraying was on both sides of the plants with the pots horizontal. One hour after spraying, each pot was filled to the brim with fine silver sand, an open-ended glass jar was placed over each pot and each pot was infested with ten hoppers. A paper tissue was placed over the open end of each glass jar to retain the hoppers. The pots were irrigated from underneath, maintained at a temperature of 27° C. ±2° C. and subjected to white fluorescent light under a regime of 18 hours light followed by 6 hours darkness. Morality assessments were made 48 hours after infestation.

(xi) *Nilaparvata lugens* (Nl)

Tests were carded out on young adult female brown rice plant hoppers in the same way as for the green leaf hoppers in (x) above.

The results are set out in Table 2 below. In Table 2 L denotes very low or no activity and ND denotes that no dam is available.

TABLE 2

| Compound | Sl Fol | Sl OA | Aa-2d | Aa-7d | Md | Af | Ap | Mv | Pc | Tv | Nc | Nl |
|---|---|---|---|---|---|---|---|---|---|---|---|---|
| 1 | <14 | 97 | L | 18 | 6 | 623 | 1900 | 154 | 10 | 840 | 3400 | 2500 |
| 2 | L | 41 | 10 | 13 | 4 | ND | 1400 | 48 | 9 | 9 | 240 | ND |
| 3 | L | L | ND | L | <1 | ND | 550 | L | L | L | 22 | ND |
| 4 | L | 14 | ND | L | L | 178 | 41 | L | L | L | 370 | ND |
| 5 | L | L | L | <3 | L | ND | 39 | L | L | L | 1200 | 5700 |
| 6 | L | <17 | L | <3 | L | ND | 160 | L | L | L | ND | ND |
| 7 | L | <13 | ND | L | L | ND | 130 | L | ND | ND | 250 | ND |
| 8 | L | <14 | ND | L | L | ND | 530 | L | 5 | 5 | 27 | ND |
| 9 | L | L | L | ND | L | ND | 420 | L | 9 | L | 600 | ND |
| C10 | L | L | L | 9 | 1 | 13 | 55 | 120 | 17 | 61 | 550 | ND |
| C11 | L | L | L | <2 | L | ND | 800 | ND | 6 | 250 | 900 | ND |

Subsequently the Ap test was re-run for Examples 1, C10 and C11, so that they would be assessed in a parallel test. The values were:
Example 1: 1000
Example C10: 92
Example C11: 330

What is claimed:

1. A process for the preparation of a compound having the formula:

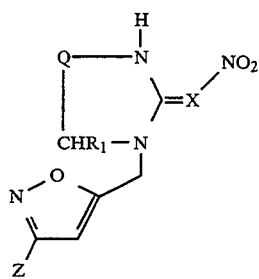

comprising:
reacting a compound of the formula

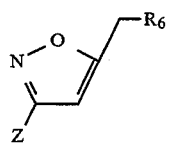

with a compound of the formula NH$_2$CHR$_1$QNH$_2$ to form an intermediary compound of the formula

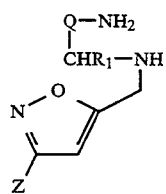

and reacting said intermediary compound with a compound having a nitromethylene or nitroimino functional group therein; wherein R$_1$ is hydrogen or alkyl; Q is a linkage group of the formula —CHR$_2$— or —CHR$_3$—CHR$_4$—, R$_2$, R$_3$, R$_4$ are independently hydrogen or alkyl; X is nitrogen or =CH—; R$_6$ is a halogen; and Z is a halogen.

2. The process of claim 1 wherein said compound having a nitromethylene functional group has the formula:

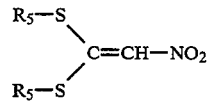

wherein R$_5$ groups are independently selected from the group consisting of C$_{1-4}$ alkyl and benzyl groups.

3. The process of claim 1 wherein said compound having a nitroimino functional group has the formula:

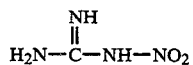

4. A process according to claim 1 having the further step of combining the product of said process with a carrier.

* * * * *